US010456070B2

(12) United States Patent
List et al.

(10) Patent No.: US 10,456,070 B2
(45) Date of Patent: Oct. 29, 2019

(54) APPARATUS FOR OBTAINING AND ANALYZING A BLOOD SAMPLE WITH A LANCET COUPLING MECHANISM

(71) Applicant: Roche Diabetes Care, Inc., Indianapolis, IN (US)

(72) Inventors: Hans List, Hesseneck-Kailbach (DE); Kai Fluegge, Aachen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 775 days.

(21) Appl. No.: 14/964,853

(22) Filed: Dec. 10, 2015

(65) Prior Publication Data

US 2016/0089069 A1  Mar. 31, 2016

Related U.S. Application Data

(63) Continuation of application No. 13/445,584, filed on Apr. 12, 2012, now abandoned, which is a (Continued)

(30) Foreign Application Priority Data

Oct. 13, 2009  (EP) ..................... 09012895

(51) Int. Cl.
*A61B 5/151* (2006.01)
*A61B 5/145* (2006.01)
*A61B 5/15* (2006.01)

(52) U.S. Cl.
CPC ...... *A61B 5/15128* (2013.01); *A61B 5/14532* (2013.01); *A61B 5/1513* (2013.01);
(Continued)

(58) Field of Classification Search
None
See application file for complete search history.

(56) References Cited

U.S. PATENT DOCUMENTS 2,801,633 A * 8/1957 Ehrlich ............ A61B 5/150022
606/181
6,409,740 B1   6/2002 Kuhr et al.
(Continued)

FOREIGN PATENT DOCUMENTS

EP   1 333 756 B1   12/2005
EP   1 790 288 A1   5/2007
(Continued)

*Primary Examiner* — Matthew Kremer
(74) *Attorney, Agent, or Firm* — Woodard, Emhardt, Henry, Reeves & Wagner, LLP (57) ABSTRACT

An apparatus for obtaining and analyzing a blood sample is presented. The apparatus comprises an integrated drive unit having a common drive source and a drive force transmission gearing that couples a lancet drive, a device for advancing a magazine, and a sample transfer device to the drive source. A tensioning rotor and a drive rotor are mounted so that they are rotatable coaxially to one another. A first cam control converts the rotation of the drive rotor into a radial forward and reverse movement of a drive rod. A second cam control converts the rotational movement of the tensioning rotor into a linear movement of a link slide. A switching link moved by the link slide rotates the magazine an additional step. A third cam control converts the rotational movement of the tensioning rotor into a linear movement of a pressure tappet perpendicular to the piercing axis.

20 Claims, 11 Drawing Sheets

Related U.S. Application Data continuation of application No. PCT/EP2010/005416, filed on Sep. 3, 2010.

(52) U.S. Cl.
 CPC .... *A61B 5/150022* (2013.01); *A61B 5/15111* (2013.01); *A61B 5/15117* (2013.01); *A61B 5/15132* (2013.01); *A61B 5/15151* (2013.01); *A61B 5/15161* (2013.01); *A61B 5/150198* (2013.01); *A61B 5/150358* (2013.01); *A61B 5/150412* (2013.01); *A61B 5/150419* (2013.01); *A61B 5/150435* (2013.01); *A61B 5/150503* (2013.01); *A61B 5/150732* (2013.01)

(56) References Cited

U.S. PATENT DOCUMENTS

| | | | |
|---|---|---|---|
| 7,740,599 | B2 | 6/2010 | Sacherer et al. |
| 7,771,367 | B2 | 8/2010 | Haar et al. |
| 7,842,060 | B2 | 11/2010 | List |
| 8,043,317 | B2 | 10/2011 | Fritz et al. |
| 2004/0092995 | A1 | 5/2004 | Boecker et al. |
| 2004/0102803 | A1 | 5/2004 | Boecker et al. |
| 2005/0015020 | A1 | 1/2005 | LeVaughn et al. |
| 2005/0245845 | A1* | 11/2005 | Roe .................. A61B 5/15173 600/583 |
| 2006/0178600 | A1 | 8/2006 | Kennedy et al. |
| 2007/0173706 | A1* | 7/2007 | Neinast ............... A61B 5/6849 600/309 |
| 2007/0191736 | A1 | 8/2007 | Raney et al. |
| 2007/0244390 | A1 | 10/2007 | Matsumura |
| 2008/0269791 | A1 | 10/2008 | Hoenes et al. |
| 2008/0300509 | A1 | 12/2008 | Hoenes et al. |
| 2009/0099477 | A1 | 4/2009 | Hoenes et al. |
| 2010/0216246 | A1 | 8/2010 | Konya et al. |
| 2010/0234869 | A1 | 9/2010 | Sacherer |
| 2011/0015661 | A1 | 1/2011 | Keil |
| 2011/0054285 | A1* | 3/2011 | Searle ............... A61M 5/14244 600/365 |
| 2011/0137205 | A1 | 6/2011 | Frey et al. |
| 2012/0039772 | A1* | 2/2012 | Hoenes .................. A61B 5/15 422/535 |

FOREIGN PATENT DOCUMENTS

| | | | |
|---|---|---|---|
| EP | 1 669 028 B1 | 1/2008 | |
| EP | 1 880 671 B1 | 9/2008 | |
| EP | 2 039 293 A1 | 3/2009 | |
| EP | 2 042 098 A1 | 4/2009 | |
| EP | 2 059 392 A1 | 4/2009 | |
| EP | 2 113 197 A1 | 11/2009 | |
| EP | 2 130 493 A1 | 12/2009 | |
| EP | 1 997 429 B1 | 11/2011 | |
| WO | WO 2003/071940 A1 | 9/2003 | |
| WO | WO 2004/060446 A2 | 7/2004 | |
| WO | WO 2004/064636 A1 | 8/2004 | |
| WO | WO 2008/145625 A1 | 12/2008 | |
| WO | WO 2008/145628 A1 | 12/2008 | |
| WO | WO 2009/027010 A1 | 3/2009 | |
| WO | WO 2009/030340 A1 | 3/2009 | |
| WO | WO-2010094428 A1 * | 8/2010 | ............... A61B 5/15 |
| WO | WO 2010/130664 A1 | 11/2010 | |

* cited by examiner

APPARATUS FOR OBTAINING AND ANALYZING A BLOOD SAMPLE WITH A LANCET COUPLING MECHANISM

CROSS-REFERENCE TO RELATED APPLICATIONS

This application is a continuation of U.S. patent application Ser. No. 13/445,584 filed Apr. 12, 2012, which is a continuation of PCT/EP2010/005416, filed Sep. 3, 2010, which is based on and claims priority to EP 09012895.0, filed Oct. 13, 2009, which are hereby incorporated by reference.

BACKGROUND

The present disclosure generally relates to an apparatus for obtaining and analyzing a blood sample and, in particular, to an apparatus for obtaining and analyzing a blood sample having a lancet coupling mechanism.

Patients with metabolic diseases typically must regularly analyze their blood. Especially diabetics are instructed to regularly check the blood sugar level. For this purpose, a small wound is generated by means of a lancet, preferably on a fingertip. A small sample is then collected from the exiting blood and transferred to a test element in order to be analyzed.

In more recent times, small, automatically operating, handheld devices have been developed, which contain a magazine having a plurality of lancets implemented as disposable articles and a corresponding number of test elements. The analysis of the blood sample is performed by an integrated measuring device. Such highly integrated devices have an advantage that the patient only needs to carry a single apparatus that can perform a number of tests identically before the consumable material needs to be replaced.

The design requirements for a small hand-held apparatus that anyone can perform an automatic blood sugar test can be extraordinarily demanding since the device needs to be as small and light as possible. It should be able to be operated so easily and comfortably that a blood sugar test can be performed anywhere and as inconspicuously as possible. Of course, absolute reliability should be expected from a medical apparatus. Since diabetes is widespread disease, the manufacturing costs should remain low for a mass-produced product.

For a fully automatically operating blood sugar test device, a special drive mechanism may be required to execute various and highly differing movements. These movements may include the rapid piercing movement of the lancet and the subsequent retraction movement, the advancing of the magazine to bring an unused lancet into functional position, the coupling of a fresh lancet and the decoupling of the used lancet, and kinematics that transfer of the blood sample from the lancet to the test element.

Therefore, there is a need for an apparatus for obtaining and analyzing a blood sample that is compact and light with very high mechanical reliability and the least possible energy demand.

SUMMARY

According to the present disclosure, an apparatus for obtaining and analyzing a blood sample is disclosed. The apparatus can comprise a housing, a contact device provided on the housing for pressing against a body part from which the blood sample is to be taken, and a magazine movably mounted on the housing. The magazine can comprise a plurality of lancets. Each lancet can pierce the body part and retract from the body part to receive the blood sample exiting the pierced body part. The apparatus further comprises a device for advancing the magazine to bring a lancet into a functional position and a lancet drive having a drive rod coupled to the lancet located in the functional position. The lancet drive can execute a controlled piercing movement along a piercing axis. Test elements can be assigned to the lancets. Each test element can receive the blood sample in order to analyze the blood sample. The apparatus also can comprise an integrated drive unit comprising the lancet drive, the device for advancing the magazine, and a device for generating a sample transfer movement perpendicular to the piercing axis.

In accordance with one embodiment of the present disclosure, the apparatus can comprise a lancet coupling mechanism. The lancing coupling mechanism can comprise at least one chamber that extends in the direction of the piercing axis and comprises a lancet, a drive rod that penetrates into the chamber and is coupled to the lancet to execute a controlled forward and reverse movement along the piercing axis. The lancet can be elastically bendable around at least one bending axis extending transversely to the piercing axis. The chamber can comprise a shaft adapted to the cross section of the lancet. The shaft can have at least one curvature around an axis transverse to the piercing axis. The drive rod can be coupled to the lancet when the lancet is in the bent state. The drive rod can have a formfitting connection to the lancet when the lancet is in a relaxed state.

Accordingly, it is a feature of the embodiments of the present disclosure to an apparatus for obtaining and analyzing a blood sample that is compact and light with very high mechanical reliability and the least possible energy demand. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

One aspect of this disclosure is an integrated drive unit that comprising a lancet drive, a device for advancing the magazine, and a device for generating a sample transfers movement substantially perpendicular to the piercing axis. The drive unit not only drives the lancet but also can ensure the advancing of the magazine at the end of a test cycle and can additionally be capable of generating a movement substantially perpendicular to the piercing axis, which can be used for the purpose of transferring the received blood sample from the lancet to an assigned test element because the lancet and the test element can be pressed against one another. A force can be exerted substantially perpendicular to the piercing axis. In addition, the sample transfer movement can comprise further movement sequences such as the test element and the lancet can be moved relative to one another. However, these movement sequences do not necessarily need to be perpendicularly to the piercing axis but rather can comprise a movement component parallel to the piercing axis, for example.

The aspect of a single drive unit for all mechanical movements needed for performing a test cycle can have many advantages. The device can be more compact and therefore lighter. In addition, the device can operate more reliably and effectively. Finally, the device may be produced cost-effectively.

In one embodiment, the integrated drive unit can have a single common drive source for delivering the force for the lancet drive, advancing the magazine, and the sample transfer movement. The drive source can be coupled to the lancet drive, the device for advancing the magazine, and the device for generating the sample transfer movement by a drive force transmission gearing. In particular, a rotor can be used as the central element of such a drive force transmission gearing. The rotor can transmit the force of the drive source selectively to the lancet drive, the device for advancing the magazine, and the device for generating the sample transfer movement as a function of the rotational angle. The movements needed for piercing, for advancing the magazine, and for sample transfer can be generated from rotational movements around a common axis.

The fact that the force of the central drive source does not directly generate the final needed required translational movements, but rather first sets a rotor into rotation, can result in a natural rotational angle range of 360° to be available so that in the course of a full rotation of the rotor to couple the drive source successively to the lancet drive, the device for advancing the magazine, or the device for generating the sample transfer movement.

It is generally known that the lancet drive should execute a rapid piercing movement in the direction of the body part which is to be pierced and a rapid subsequent retraction movement, at least at the beginning. In comparison, the remaining movements that are required for advancing the magazine, for coupling and decoupling the lancet, and for transferring the blood sample from the lancet to the test element, are relatively slow. For this purpose, the drive unit can advantageously comprises a drive rotor whose rotation is converted by a first cam control into a radial forward and reverse movement of the lancet, a coaxial tensioning rotor, a drive spring acting between drive rotor and tensioning rotor, and also a stepping switch mechanism having a second cam control that converts the rotational movement of the tensioning rotor into a linear movement for advancing the magazine, as well as a test element coupling device having a third cam control that converts the rotational movement of the tensioning rotor into a linear movement of a contact pressure element perpendicular to the piercing axis. According to one embodiment, only the tensioning rotor can be directly frictionally coupled to the central drive source via the drive force transmission gearing. A rotation of the tensioning rotor is converted by the cam controls either into a linear movement for advancing the magazine or into a linear movement of a contact pressure element perpendicular to the piercing axis. The slow movements may thus be implemented. The rapid piercing movement of the lancet can occur if the drive spring was previously tensioned, by rotating the tensioning rotor in relation to the drive rotor, and released to trigger the piercing. In this manner, it can be possible to adapt the drive source primarily to the slow movements of the magazine, the lancet coupling mechanism, and the device for blood sample transfer. The substantially more rapid piercing movement can be triggered by the tension force of the drive spring. Because the tensioning rotor can be used as the central element of the drive force transmission gearing, it can be possible to cause all movements of the drive mechanism to arise from a single common drive source.

An electric motor can be suitable for the drive source where the speed can optionally be stepped down by means of a worm gearing sufficiently so that the rotational movement of the tensioning rotor can be sufficiently controlled precisely. However, any other moving drive element which delivers a mechanical drive force, such as a spring mechanism for example, can also be used. The drive source can also comprise an energy accumulator.

Another aspect of the present disclosure is a lancet coupling. The flexibility of the lancet in conjunction with the curved chamber can result in the lancet stored in the chamber can be elastically bent with the curvature of the chamber. Because of the bending tension, the lancet can be clamped in the chamber. The lancet can thus press against the wall of the chamber with spring force. This can have the advantage that the lancet in the chamber can remain in position even if the chamber is moved or shocks are exerted thereon. Rattling noises during the transport and handling of the device can be prevented.

If the lancet is withdrawn from the curved chamber along the piercing axis, it can relax and reassume its original shape. The elastic deformation of the lancet during the transition from the bent state into the relaxed state and vice versa can be used to couple the drive rod to the lancet. The drive rod can be coupled onto the lancet when the lancet is in the bent state. In contrast, if the lancet is in the relaxed state outside the chamber, the drive rod can have a formfitting connection to the lancet. A controlled piercing movement can now be executed along the piercing axis. The form fit between drive rod and lancet can also allow the lancet to be retracted again after the piercing. If the lancet is retracted sufficiently far enough that it enters the curved shaft of the chamber again, the lancet can again bend elastically. The formfitting connection between lancet and drive rod may thus be disengaged again.

To produce the formfitting connection in the relaxed state, the lancet can have a coupling recess and the drive rod can have a coupling structure on its front end that can extend perpendicular to the bending axis of the lancet and that can engage in the coupling recess of the bent lancet. If the lancet is withdrawn from the chamber, the coupling recess can move on a circular path around the bending axis. In contrast, the coupling structure can only move in the direction of the piercing axis. During synchronous movement of drive rod and lancet in the direction of the piercing axis, a relative movement can result between the coupling recess and the coupling structure in a direction perpendicular to the piercing axis. The coupling recess therefore can automatically engage with the coupling structure.

The lancet can be manufactured simply from a piece of level flat sheet metal. It can have an eye in a rear area. The drive rod can have a correspondingly implemented hook in a front end, which can hook into the eye of the lancet. The lancets, of which large quantities may be required, can be produced very simply and cost-effectively, for example, by stamping. It may only be necessary to select a sufficiently elastic material, such as, for example, sheet steel. The eye should be sufficiently wide that the hook at the front end of the drive rod can be hooked on. In one embodiment, the lancets can be approximately 1 mm wide. The chamber for accommodating the lancet can be implemented as correspondingly narrow.

A plurality of chambers may be positioned adjacent to one another in a circular magazine, the shafts of the chambers extending in the radial direction. By rotating the magazine, one of the chambers may be brought into a position in which the drive rod can penetrate into the chamber and can couple onto the lancet located into the chamber. Such an arrangement of the chambers in a flat ring magazine allows the construction of a very compact handheld device having low overall height, above all if a rotor drive is positioned coaxially in the middle of the ring magazine.

In one embodiment, the magazine can comprise a lower part and an upper part which can form the chambers. The lancets may thus be laid in the relaxed state in the still open chambers. As soon as the upper part is put on, the lancets can be forced into the curvatures of the resulting shafts and can no longer slip out of their predefined position inside the magazine without force from the outside. All chambers of the magazine can be filled simultaneously with lancets in one work step and the bending of the lancets which is required for the function of the lancet coupling mechanism can be generated by simply pressing on the magazine upper part.

Figure 1:
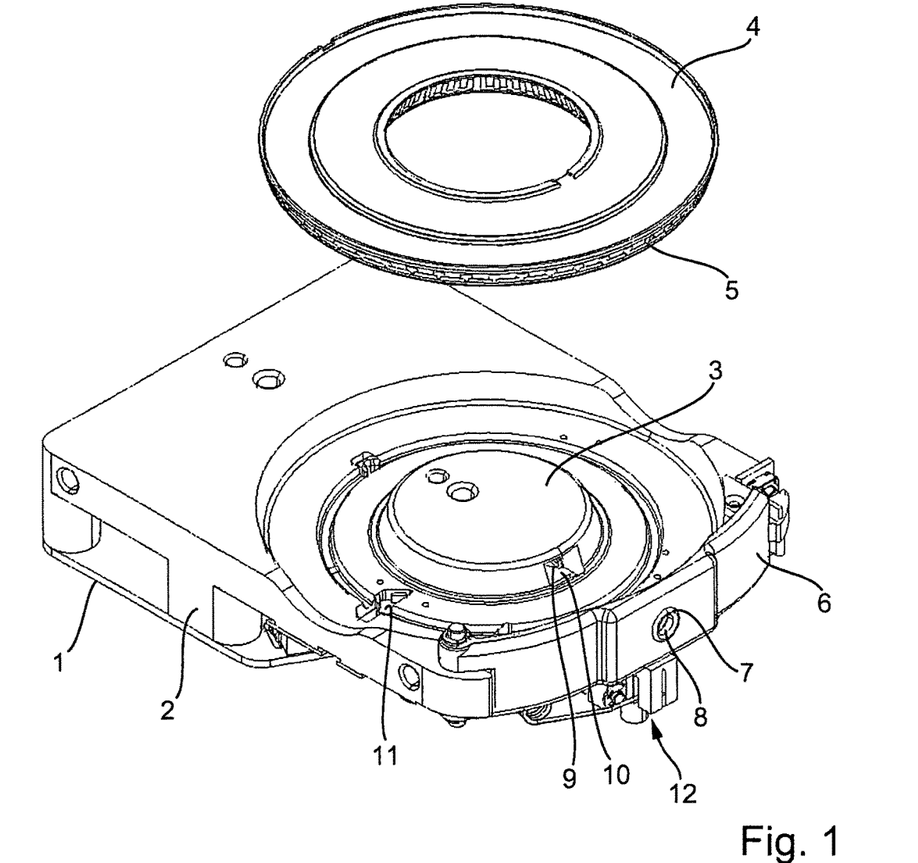
FIG. 1 illustrates an apparatus for obtaining and analyzing a blood sample in a simplified perspective view according to an embodiment of the present disclosure.

Referring now to FIG. 1, the load-bearing element of the apparatus can be a base plate 1. The housing can comprise an upper cover 2 can be installed on the base plate 1. A round receptacle 3 can be provided on the upper side on which a magazine 4 in the form of a circular ring can be placed. This magazine 4 can comprise a plurality of chambers 5 in each of which a lancet is stored. The chambers 5 can be positioned adjacent to one another and can extend in the radial direction. The magazine 4 can also comprise a plurality of test elements assigned to the chambers 5.

The front side of the housing can be formed by a contact pressure bow 6. A fixation ring 7 with an opening 8 can be positioned approximately in the middle of the contact pressure bow 6. The fixation ring 7 can be used for the contact pressure of a body part, such as a fingertip, from which a blood sample is to be taken. The fingertip can protrude somewhat into the opening 8. One of the lancets stored in the magazine 4 can pierce through the opening 8 into the fingertip and can be retracted again to get a sample of the blood from the puncture wound.

The lancet drive can be concealed under the cover 2. Only the front end of a drive rod 9, is visible through a rectangular exit opening 10 in the cover 2 in FIG. 1. In operation, when the magazine 4 is positioned in the receptacle 3, the drive rod 9 can emerge from the opening 10 and penetrate the rear of a chamber 5 of the magazine 4 to drive the lancet stored therein forward in the direction of the opening 8 and subsequently withdraw the lancet again along the piercing axis into the chamber 5. The blood sample can be transferred to a test element for analysis.

The lancets and test elements stored in the magazine 4 are intended for a single use. After obtaining and analyzing a blood sample, the magazine 4 can be rotated around its axis to move a fresh lancet into the functional position. The device for advancing the magazine 4 can be located below the cover 2. A link slide 11 can cooperate with pins provided on the lower side of the magazine 4 in order to convert a movement of the link slide 11 in the radial direction into a rotation of the magazine 4 around its rotational axis.

A device 12 for generating a sample transfer movement perpendicular to the piercing axis can be seen below the contact pressure bow 6. This device 12 can be used to transfer the blood sample received by the lancet onto an assigned test element in the magazine 4 since that the lancet and the test element can be pressed against one another.

Figure 2:
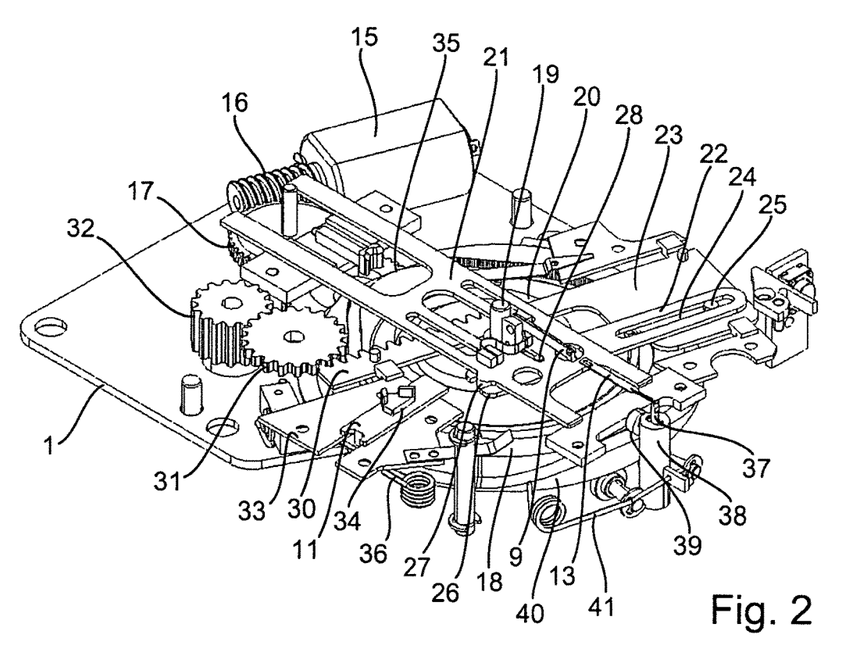
FIG. 2 illustrates the drive unit of the apparatus of FIG. 1 in perspective with an enlarged scale according to an embodiment of the present disclosure.

The details of the drive unit can be seen in FIG. 2. A lancet 13 can be located in the functional position in front of the drive rod 9. An electric motor 15 can be fastened on the base plate 1 and can be supplied with power by a battery. A worm shaft 16, which can be meshed with a worm wheel 17, can be positioned on the shaft of the electric motor 15. The speed of the electric motor 15 can be stepped down strongly. Further gearwheels, which can be partially located below the base plate 1, can transmit the drive force of the electric motor 15 to a tensioning rotor 18 mounted so it can be rotatable around a perpendicular rotational axis 19 on the base plate 1. A drive rotor 20 can be mounted so it is rotatable around the same rotational axis 19 and therefore coaxially to the tensioning rotor 18. Tensioning rotor 18 and drive rotor 20 can be connected so they are rotationally movable via a coiled spring. This coiled spring can be used as the drive spring of the lancet drive.

If the tensioning rotor 18 is set into rotation by the electric motor 15 while the coaxial drive rotor 20 is stationary, the drive spring can be tensioned. If the drive rotor 20 is then released, it runs behind the tensioning rotor 18 under the action of the relaxing drive spring. This rapid rotation of the drive rotor 20 can be converted by a cam control into a radial forward and reverse movement of a piercing carriage 21. The piercing carriage 21 can carry a drive rod 9 which can be coupled onto a lancet.

In order to vary the stroke of the lancet, the rotation of the drive rotor 20 cannot be directly converted into a radial forward and return movement of the lancet along the piercing axis. Rather, the conversion can be performed via a one-armed transmission lever 22, whose lever axis is mounted on a lever carriage 23 movable transversely to the piercing axis. The transmission lever 22 can have a substantially oblong hole 24 in which a pivot pin 25 of the lever carriage 23 engages. On its opposite free end, the transmission lever 22 can be implemented as a fork 26, which encompasses a pin 27 provided at the edge of the piercing carriage 21. Pivoting the transmission lever 22 around a pivot pin 25 therefore can result in a linear movement of the piercing carriage 21 along the piercing axis or in the radial direction, in relation to the rotational axis 19 of the drive rotor 20.

Between the oblong hole 24 and the fork 26, the transmission lever 22 can carry a groove rider 28, which points downward and engages in a control groove 29 provided on the upper side of the drive rotor 20. If the lever carriage 23 is moved to the left, for example, the pivot pin 25 can travel to the right in the oblong hole 24. The lever arm between pivot pin 25 and groove rider 28 can thus be lengthened, and therefore the transmission ratio using which a radial movement of the groove rider 28 can be transmitted via the transmission lever 22 to the pin 27 of the piercing carriage 21. Since the lever carriage 23 is displaced parallel to the rest location of the transmission lever 22, only the stroke of the free lever end which drives the piercing carriage 21 changes, while in contrast, the rest position of the piercing carriage 21 is not changed. This can allow the stroke of the lancet to be varied in order to adapt the piercing depth.

The rear edge of the lever carriage 23 can be implemented as a tooth rack 30 in which a gearwheel 31 engages. The drive can be performed by a gear pinion 32. Therefore, the lever carriage 23 can be moved right or left to set the transmission ratio of the transmission lever 23.

The drive unit can integrate a stepping switch mechanism having a second cam control, which converts the rotational movement of the tensioning rotor 18 into a linear movement for advancing the magazine 4. The stepping switch mechanism can comprise the link slide 11, which is mounted so it is movable in the radial direction on a guide 33. The link slide 11 can carry a switching link 34 on its upper side. Correspondingly shaped switching pins can be provided on the lower side of the magazine 4, which engage in the switching link 34 from above to convert the radial movement of the link slide 11 into a limited rotational movement of the magazine 4. The tensioning rotor 18 can carry a switching cam 35 on its outer side. A spring bow 36 presses an actuating element of the link slide 11 against the outer side of the tensioning rotor 18. As it travels over the switching cam 35, the link slide 11 can follow the curved path formed by the switching cam 35 so that the rotational movement of the tensioning rotor 18 can be converted into a linear forward and reverse movement of the link slide. This short-stroke movement can be transmitted by the switching link 34 to the magazine 4 in order to rotate it one step further. Therefore, the next chamber 5 having a new lancet can reach the functional position.

Further, the drive unit can comprise a device for generating a sample transfer movement perpendicular to the piercing axis. A pressure tappet 37 can be mounted so it is vertically movable in a friction sleeve 38 at a small distance from the edge of the tensioning rotor 18. The pressure tappet 37 can be connected to a friction roller 39. A ramp 40, which the friction roller 39 travels on the upper side of, can be implemented on the tensioning rotor 18 in the area of the outer edge. If the tensioning rotor 18, driven by the electric motor 15, is set into slow rotation, the friction roller 39 can reach the area of the ramp 40 at a specific angle of the tensioning rotor 18 and can begin to be displaced upward. The pressure tappet 37 can thus move upward. After reaching the apex of the ramp 40, the friction roller 39 and the pressure tappet 37 can move back downward.

The movement executed by the pressure tappet 37 can extend perpendicularly to the piercing axis, but can also comprise a movement component parallel to the piercing axis. The movement of the pressure tappet 37 can be used for pressing the active lancet against a test element after the piercing in order to transfer the blood sample. The pressure tappet 37 can subsequently retract again, whereby the lancet disengages again from the test element. A spring bow 41 can ensure that the friction roller 39 is spring-loaded against the upper side of the ramp 40 so that it can ensure that the friction roller 39 precisely follows the contour of the ramp 40.

The drive unit generates from the movement of a common central drive source, for example, the electric motor 15, all of the manifold movements required for obtaining and analyzing a blood sample. The force of the electric motor 15 can be transmitted by a Y-shaped branched drivetrain to the lancet located in the functional position, the magazine 4, and the device for generating a sample transfer movement perpendicular to the piercing axis. The central element of this drive force transmission gearing can be the tensioning rotor 18 which selectively distributes the force of the electric motor 15 as a function of its rotational angle, specifically for tensioning the drive spring of the lancet drive, for actuating the link slide 32, or for raising the pressure tappet 37.

Figure 3A:
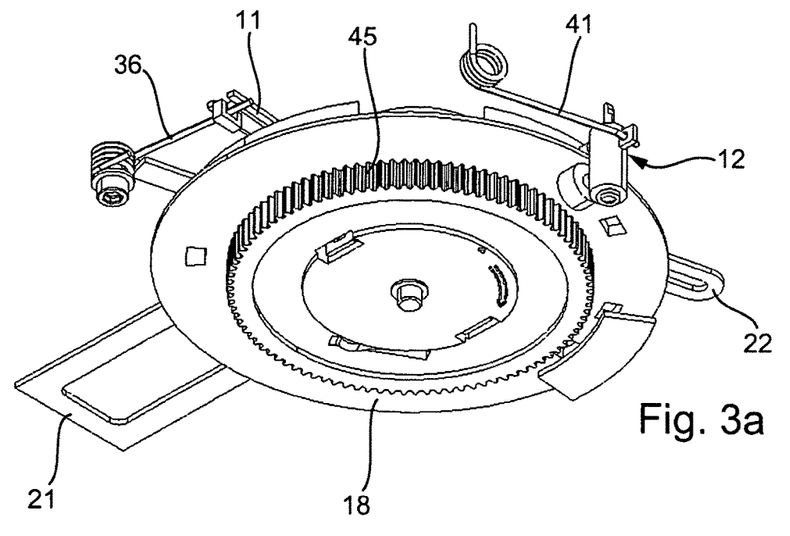
FIG. 3a illustrates a view from below of the tensioning rotor of the drive unit of FIG. 2 according to an embodiment of the present disclosure.
Figure 3B:
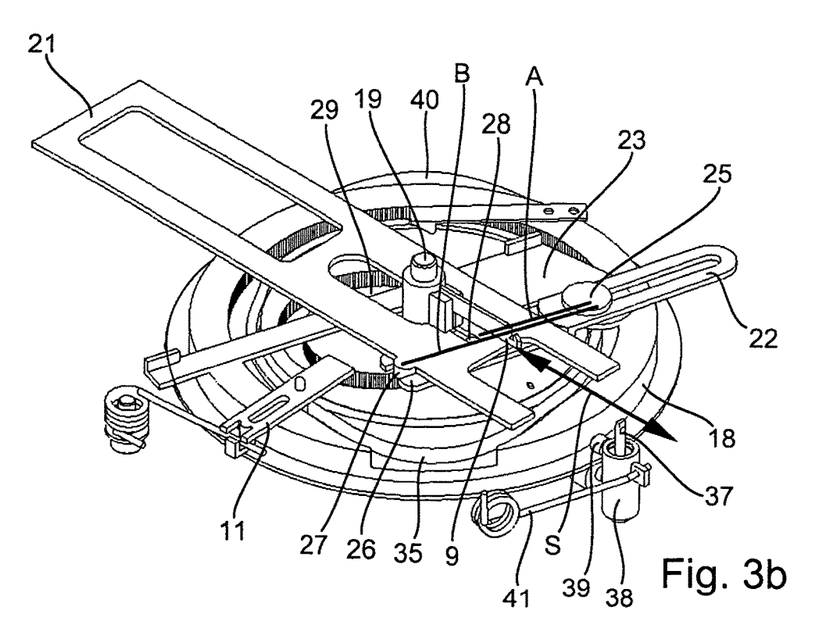
FIG. 3b illustrates a view from above of the tensioning rotor of the drive unit of FIG. 2 according to an embodiment of the present disclosure.

In FIGS. 3a and 3b, the drive unit is shown reduced to the moving elements for better understanding. The common rotational axis 19, around which the tensioning rotor 18 and the drive rotor 20 rotate, can be positioned in the middle. On its lower side (see FIG. 3a), the tensioning rotor 18 can have a gear ring 45, via which the drive force of the electric motor 15 is transmitted to the tensioning rotor 18. The gearwheel engaging in the gear ring 45 is omitted in this figure, as are the remaining elements of the drive force transmission gearing, which frictionally connects the tensioning rotor 18 to the electric motor 15.

Figure 4:
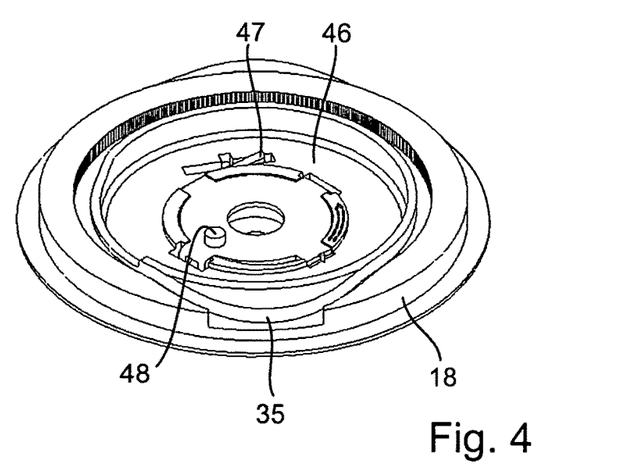
FIG. 4 illustrates the tensioning rotor from above according to an embodiment of the present disclosure.

The tensioning rotor 18 can have the basic shape of a flat disk and can have a central pot-like recess 46, seen best in FIG. 4. The drive rotor 20, which can be a flat circular disk, best seen in FIGS. 5a and 5b, can be seated in this recess 46. A pawl 47, which can be a rocker, can be mounted so it is pivotable on the base of the pot-like recess 46 of the tensioning rotor 18. A curved groove 49 for the engagement of the locking pin 48 and a recess 50, in which the pawl 47 can engage, can be provided corresponding to the lower side of the drive rotor 20. The tensioning rotor 18 and the drive rotor 20 may thus alternately be connected rotationally fixed to one another in one rotational direction or can also latch rigidly with one another. If tensioning rotor 18 and drive rotor 20 are connected rotationally fixed to one another by means of pawl 47 and locking pin 48, a rotational movement of the tensioning rotor 18 can be transmitted directly to the drive rotor 20, so that it can also execute slow movements, as may be needed before and after a piercing.

Figure 5A:
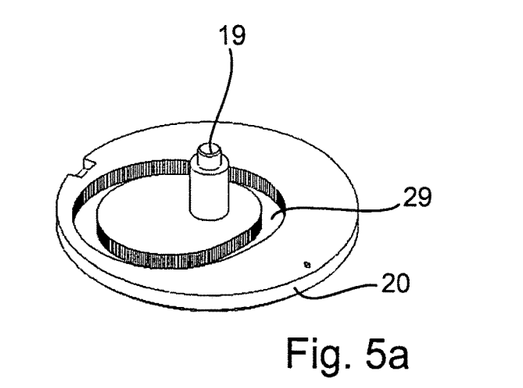
FIG. 5a illustrates the drive rotor of the drive unit of FIG. 2 from above according to an embodiment of the present disclosure.
Figure 5B:
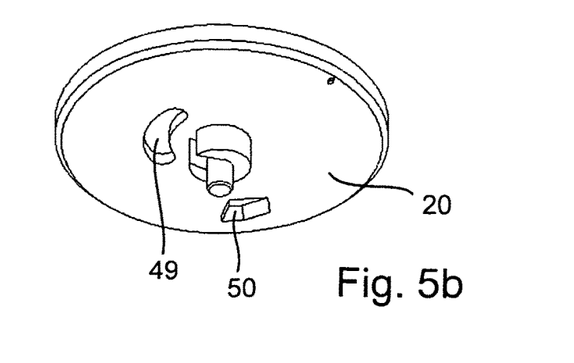
FIG. 5b illustrates the drive rotor of the drive unit of FIG. 2 from below according to an embodiment of the present disclosure.

FIG. 3b also illustrates the function of the transmission lever 22, whose groove rider 28 travels down the control groove 29 of the drive rotor 20 (see FIG. 5a). The transmission lever 22 can be mounted by the pivot pin 25 on the lever carriage 23, the oblong hole 24 permitting a movement of the lever carriage 23 transversely to the piercing axis S. The piercing carriage 21 having the drive rod 9 installed thereon can engage with its pin 27 in the fork 26 of the transmission lever 22. The transmission ratio, which is settable by moving the lever carriage 23, can result from the ratio between short lever arm A and long lever arm B, the short lever arm A corresponding to the distance between groove rider 28 and rotational axis of the pivot pin 25 and the long lever arm B corresponding to the distance between pivot pin 25 and engagement point of the fork 26 on the pin 27.

The conversion of the rotational movement of the tensioning rotor 18 into a second linear movement, which can be used for advancing the magazine 4 (see FIG. 2), can be performed by a switching cam 35, which is visible at the angle of the tensioning rotor 18 shown in FIG. 3b. A friction pin 51, which is provided on the lower side of the link slide 11, can travel down the switching cam 35. The spring bow 36 can ensure a springy contact of the friction pin 51 on the edge side of the tensioning rotor 18.

The outer edge of the tensioning rotor 18 can be implemented as a flat flange pointing outward, similar to a brim of a hat. This edge can be thickened to a multiple of its thickness in the area of the ramp 40. If the friction roller 39 travels down the ramp 40, the pressure tappet 37 mounted in the friction sleeve 38 can move perpendicularly upward to execute a sample transfer movement. The spring bow 41 can ensure a uniform contact pressure by using the friction roller 39 pressing on the edge of the tensioning rotor 18, in particular as it travels over the ramp 40.

Figure 6:
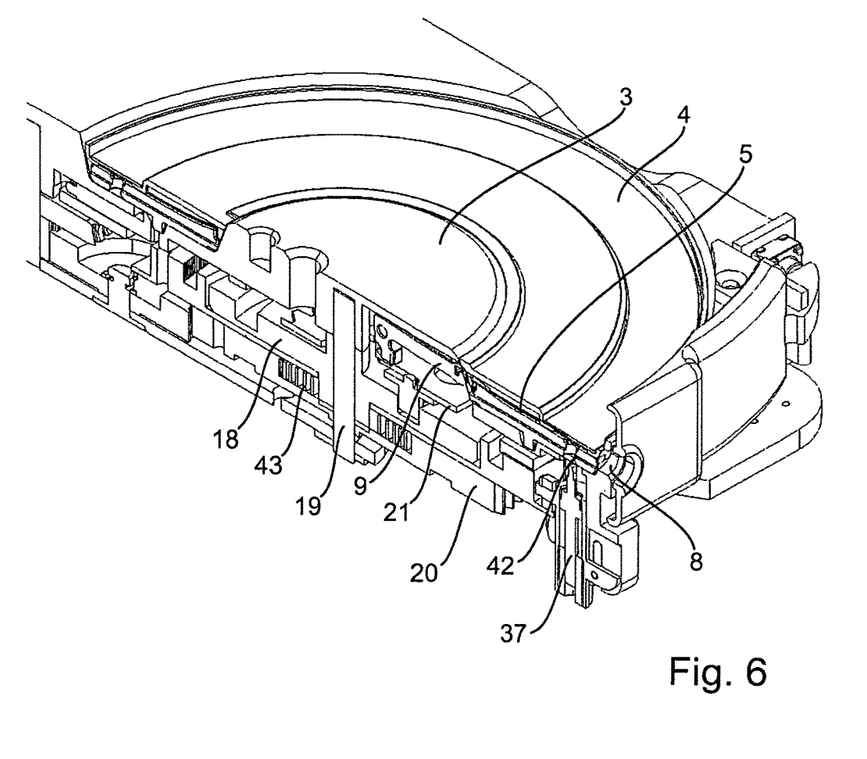
FIG. 6 illustrates a part of the apparatus of FIG. 1 having an inserted magazine in an enlarged perspective view with vertical section in the radial direction through the rotational axis according to an embodiment of the present disclosure.

In FIG. 6, the magazine 4 is seated on the receptacle 3. The common rotational axis 19, around which the tensioning rotor 18, the drive rotor 20, and the magazine 4 rotate is visible. The vertical section of FIG. 6 goes centrally through one of the chambers 5 positioned in a ring that are used to accommodate disposable lancets. The chamber 5 can extend in the radial direction in relation to the rotational axis 19. The drive rod 9 installed on the piercing carriage 21 can still be located completely outside the chamber 5, but can penetrate into the rear of the chamber 5 to execute a piercing, in order to couple onto the lancet stored therein and drive it forward in the radial direction in the direction of the opening 8.

The function of the pressure tappet 37 shown in FIG. 6 can be to penetrate through an entry opening 42 from below into the chamber 5, in order to bring the lancet into contact with a test element after the piercing. Furthermore, the drive spring 43 is visible seated between tensioning rotor 18 and drive rotor 20.

Figure 7A:
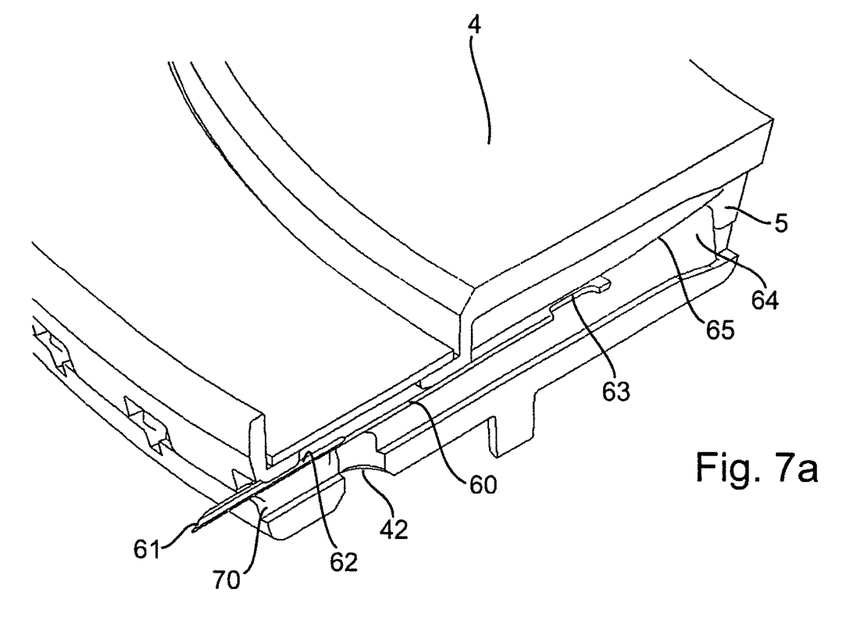
FIG. 7a illustrates the magazine of the apparatus of FIG. 1 with lancet in a simplified perspective view in longitudinal section through a chamber according to an embodiment of the present disclosure.

In FIG. 7a, a lancet 60 is partially located in the chamber 5. The lancet 60 can be manufactured from a piece of level flat sheet metal which can be elastically bendable around a bending axis extending transversely to the piercing axis. Because FIG. 7 extends along the longitudinal axis of the lancet 60, only one half of the lancet 60 is visible. The other half is implemented in a mirror image. At the front, the lancet 60 can be ground sharp and can form a tip 61 which can be adjoined by a capillary trough 62 for receiving the blood sample. In the rear area, the lancet 60 can have an eye 63 to couple to the drive rod 9 (see FIG. 6).

The chamber 5 can have a shaft 64 adapted to the cross section of the lancet 60. In one embodiment in which the lancet can be manufactured from a level flat sheet metal, the shaft 64 can have a substantially rectangular cross section having a height which can be minimally greater than the thickness of the lancet 60, which can slide back and forth with some play in the shaft 64. In the rear area, which points radially inward, the shaft 64 can have a curvature 65 which extends along the piercing axis.

Figure 7B:
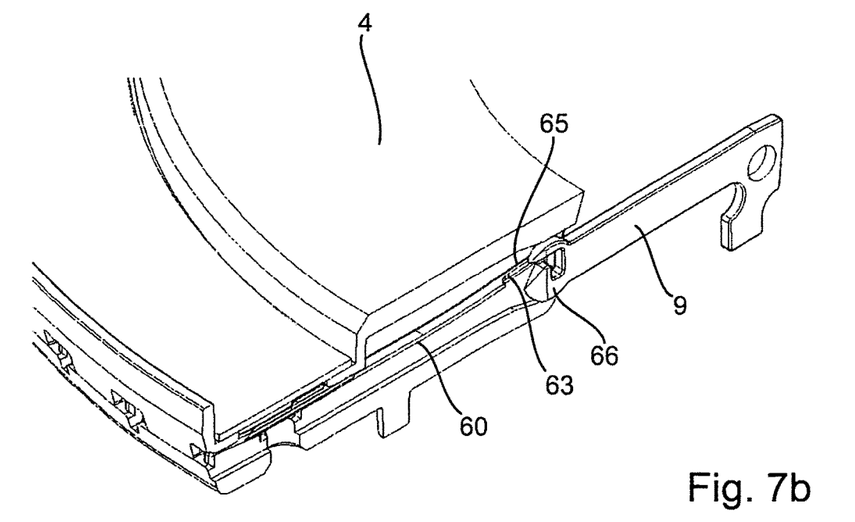
FIG. 7b illustrates the magazine according to FIG. 7a with lancet and drive rod of the drive unit of FIG. 2 according to an embodiment of the present disclosure.

FIG. 7b illustrates the cooperation between the chamber 5 having curved shaft 64, the elastically bent lancet 60, and the drive rod 9, which has just entered the rear end of the chamber 5 here. In FIG. 7a, the lancet 60 is visible still in the level relaxed state. If the lancet 60 is now pushed inward, starting from this location, in the radial direction, it can follow the curvature 65 of the shaft 64 and bend elastically. The eye 63 can simultaneously be displaced vertically upward. Vice versa, if the lancet 60 is pushed radially outward, the eye 63 can again be displaced vertically downward. This displacement may be used for coupling and decoupling the drive rod 9, for which purpose the drive rod 9 has a corresponding coupling structure.

Figure 8:
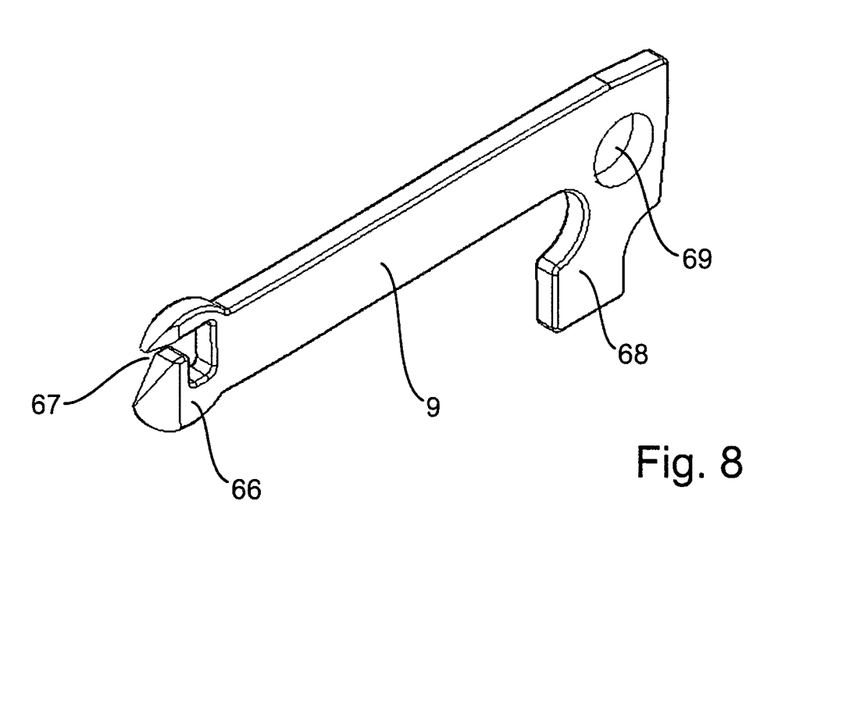
FIG. 8 illustrates the drive rod of FIG. 7b, in a greatly enlarged perspective view according to an embodiment of the present disclosure.

According to FIG. 8, the drive rod 9 has a hook 66 on its front end, which can be hooked into the eye 63 of the lancet 60 (see FIG. 7a). The slot 67 in the hook 66 can be just large enough that the rear of the lancet 60 can fit through it. On its rear end in the piercing direction, the drive rod 9 can have a shaft 68 with a fastening hole 69. The drive rod may thus be installed on the piercing carriage 21 (see FIGS. 2 and 6).

The drive rod 9 can be manufactured from a single piece of sheet steel. The drive rod 9 can be significantly narrower than the lancet 60. To guide the drive rod 9 in the chamber 5, its shaft 64 can have a central guide groove 70, whose height and width can be adapted to the dimensions of the drive rod 9 (cf. FIG. 7b). The relatively narrow drive rod 9 can thus run in the middle of the shaft 64 without the drive rod 9 having to follow the curvature 65, which can only engages on the right and left on the lancet 60.

The elastically bendable lancet 60 having eye 63, the chamber 5 having shaft 64 and curvature 65, and the drive rod 9 having hook 66 can form a lancet coupling mechanism in which the lancet 60 can automatically couple onto the drive rod 9 when the drive rod 9 penetrates into the chamber 4 and drives the lancet 60 radially outward.

Figure 9A:
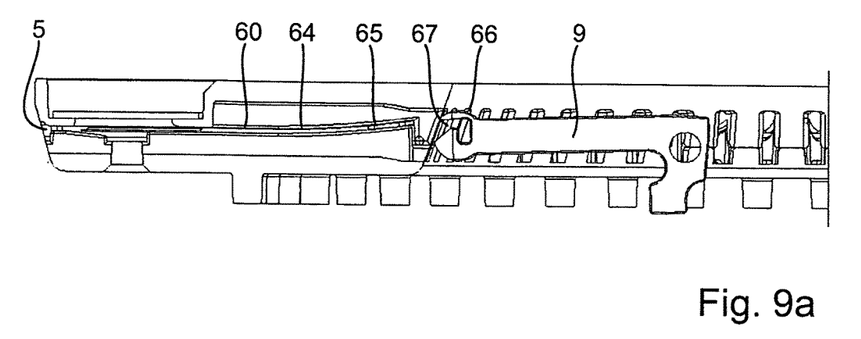
FIGS. 9a-d schematically illustrate the procedure of coupling the drive rod onto a lancet according to an embodiment of the present disclosure.

The coupling of the drive rod 9 onto the lancet 60 in the preparation phase of a piercing will be described in FIGS. 9a-d. In FIG. 9a, the drive rod 9 can still be located outside the chamber 5. The lancet 60 can be located completely in the shaft 64. The rear area of the lancet 60 can be bent by the curvature 65 perpendicularly out of the sheet metal plane, upward in the figure. The rear of the lancet 60 can therefore protrude beyond the slot 67 of the hook 66 of the drive rod 9.

Figure 9B:
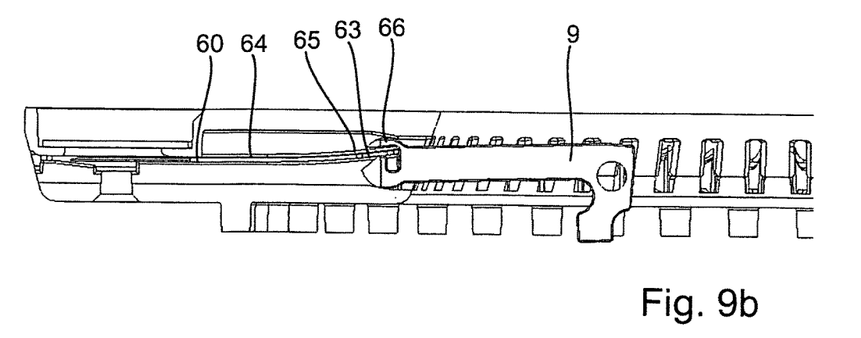

In FIG. 9b, the drive rod 9 has moved a small distance outward in the radial direction (to the left in the figure), it having penetrated from the rear into the chamber 5. The rear of the lancet 60 can slip through the slot 67 of the hook 66, so that the hook 66 can now engage in the eye 63 from below. The hooking of the eye 63 can be assisted by the spring tension of the elastically bent lancet 60. If the drive rod 9 penetrates further into the chamber 5, it can drive the lancet 60 further in the radial direction outward out of the chamber 5. This is the rapid piercing movement to generate a small wound.

Figure 9C:
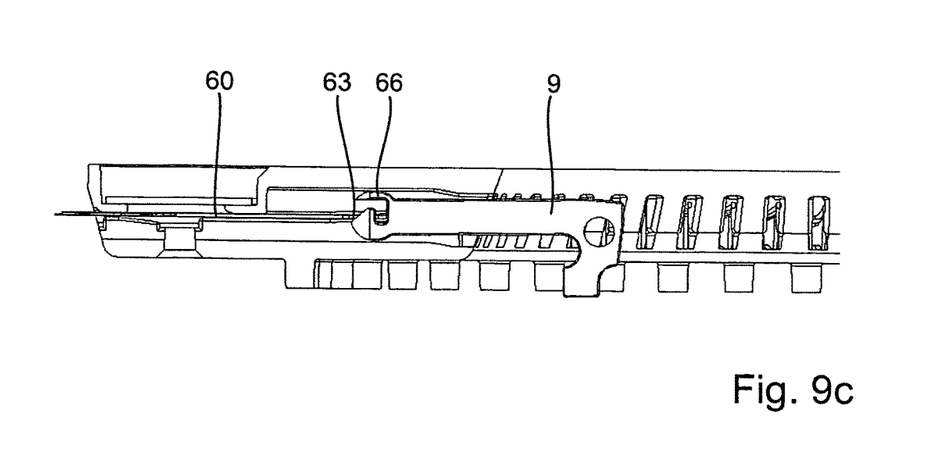

In FIG. 9c, the lancet 60 has left the area of the curvature 65 (see FIG. 9b). The lancet 60 can now be in the relaxed state and the hook 66 can completely be hooked in the eye 63.

Figure 9D:
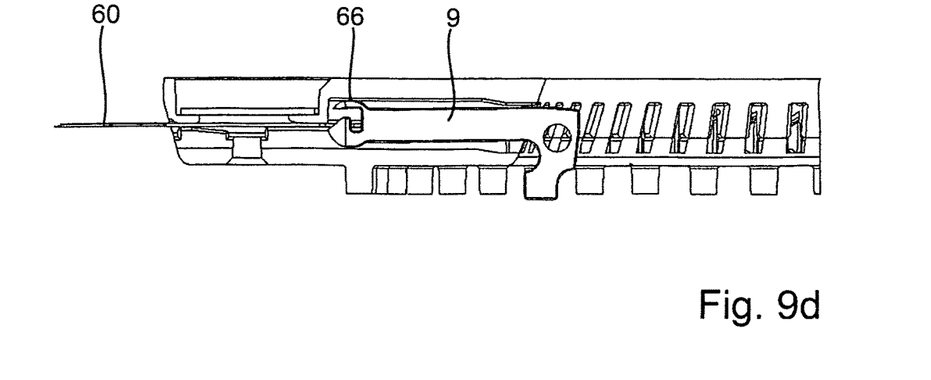

In FIG. 9d, the lancet 60 has reached its reversal point. This corresponds to the maximum piercing depth. The movement direction of the drive rod 9 can now be reversed. The undercut of the hook 66 can allow the drive rod 9 not only to press the lancet 60 forward, but also pull it to the rear, the formfitting connection between hook 66 and eye 63 being maintained. In the course of the further retraction of the drive rod 9 and the appended lancet 60, the lancet can finally be automatically decoupled upon entering the area of the curvature 65. The procedure of decoupling can precisely correspond to the described coupling, but in the reverse direction. FIG. 9b can correspond to the moment at which the hook 66 releases the eye 63 again.

Figure 10:
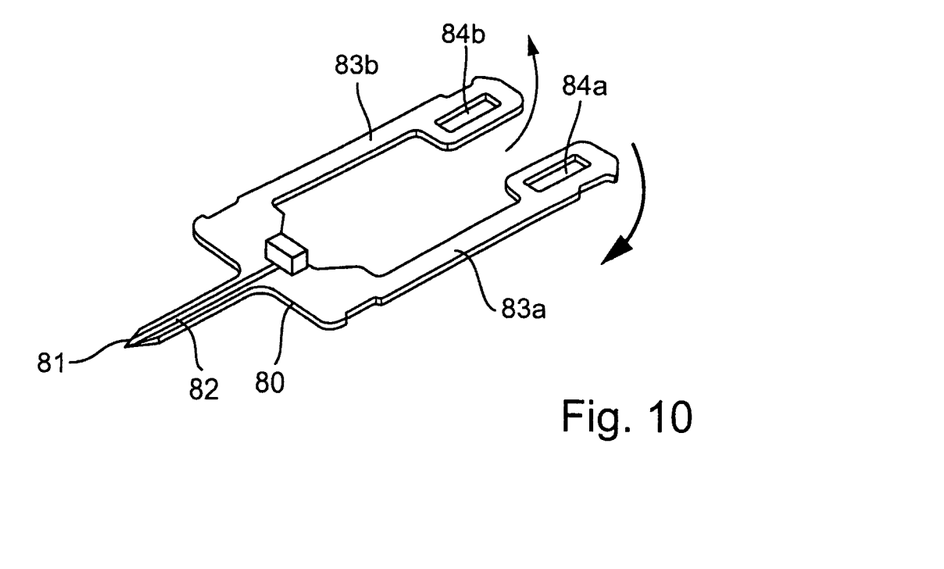
FIG. 10 illustrates an alternative embodiment of the lancet according to an embodiment of the present disclosure.

The alternative embodiment of a lancet 80 according to FIG. 10 also has a tip 81 and a capillary trough 82 adjoining thereon. In contrast to the above-described lancet, the body of the lancet 80 can be divided into two arms 83a and 83b, which can be implemented as mirror images. An eye 84a or 84b can be provided in the area of the end in each case, which can be used to couple on a drive rod equipped with two parallel hooks. This lancet 80 can also be produced from a piece of level sheet metal that can be elastically bendable. The one arm 83a may be bent elastically upward around a bending axis extending transversely to the piercing axis while the other arm 83b can be bent downward in the opposite direction. To store the lancet 80 in a magazine, the magazine chambers can each comprise a right shaft and a left shaft, one shaft being curved upward and the other shaft being curved downward.

Figure 11:
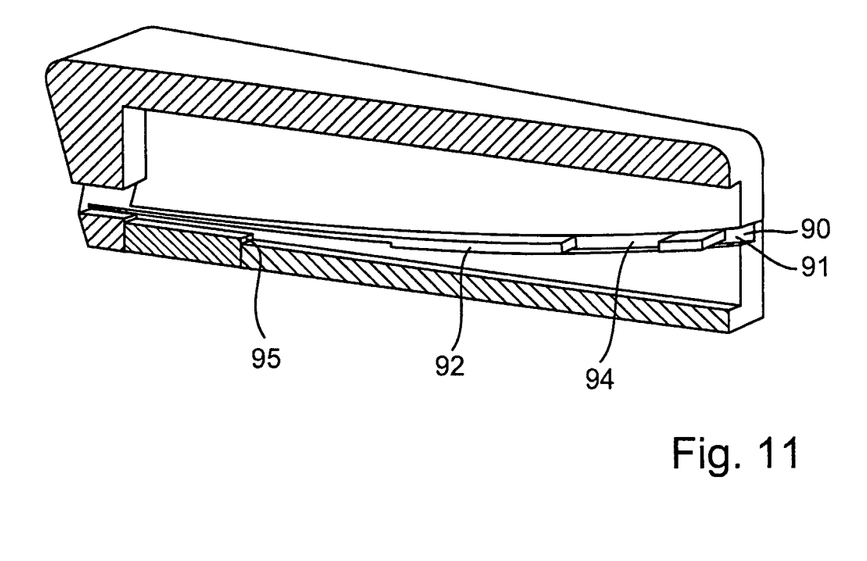
FIG. 11 illustrates an alternative embodiment of a lancet coupling mechanism according to an embodiment of the present disclosure.

The alternative embodiment of a lancet coupling mechanism shown in FIG. 11 can have a magazine chamber 90 having a shaft 91, which can be curved over its entire length around an axis transverse to the piercing direction. The lancet 92 inserted into the shaft 91 can correspondingly be elastically bent on its entire length and therefore also in the front area (on the left in the figure). An eye 94, which can provided close to the rear of the lancet 92 and can move downward upon a movement of the lancet 92 in the piercing direction (to the left in the figure) in accordance with the curvature of the shaft 91, can again be used for coupling and decoupling the lancet 92 onto and from a drive rod. Because of the bending tension, the tip 93 of the lancet 92 can therefore be pressed downward and can be incident on a test panel 94 positioned directly below the shaft 91. In this way, the blood received by the lancet 92 during a piercing procedure can be automatically transferred onto the test panel 95 without a further aid being required.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A lancet coupling mechanism for an apparatus for obtaining and analyzing a blood sample, comprising:
   a lancet having an eye;
   at least one chamber, which extends in a direction of a piercing axis, wherein the chamber contains the lancet;
   a drive rod, which penetrates into the chamber for coupling onto the lancet, in order to execute a controlled forward and reverse movement of the lancet along the piercing axis, wherein the drive rod has at least one hook;
   at least one bending axis of the lancet that extends transverse to the piercing axis; wherein the lancet is elastically bendable from a relaxed state to a bent state around the bending axis;
   wherein at least in a rear area of the chamber comprises a shaft that has at least one curvature that curves around the bending axis;
   wherein the shaft guides the controlled forward and reverse movement of the lancet; wherein the curvature at the rear area of the chamber is configured to bend the lancet from the relaxed state to the bent state; and
   wherein the drive rod is configured to push the lancet out of the curvature at the rear area of the chamber to hook the hook of the drive rod into the eye of the lancet.

2. The lancet coupling mechanism according to claim 1, wherein the hook of the drive rod extends perpendicularly to the bending axis of the lancet and engages in the eye of the bent lancet when the lancet moves forward.

3. The lancet coupling mechanism according to claim 2, wherein the lancet is manufactured from a piece of level flat sheet metal.

4. The lancet coupling mechanism according to claim 1, wherein the shaft has a central guide groove, whose height and width are adapted to the dimensions of the drive rod.

5. The lancet coupling mechanism according to claim 1 wherein the shaft has a rectangular cross section having a height which is greater than a thickness of the lancet, which is slidable back and forth with play in the shaft.

6. The lancet coupling mechanism according to claim 1, wherein the drive rod is manufactured from a single piece of sheet steel.

7. The lancet coupling mechanism according to claim 1, wherein:
   the lancet includes a body;
   the body of the lancet comprises two arms, which are implemented as mirror images; and the eye includes at least two eyes that are provided at the end of the two arms, respectively.

8. The lancet coupling mechanism according to claim 7, wherein one of the two arms is bent elastically upward around the bending axis extending transversely to the piercing axis, while the other of the two arms is bent elastically downwards in the opposite direction.

9. The lancet coupling mechanism according to claim 8, wherein the chamber comprises a right shaft and a left shaft, one shaft being curved upward and the other shaft being curved downward.

10. The lancet coupling mechanism according to claim 1, wherein the shaft is curved over an entire length of the shaft around the bending axis; and
the lancet inserted into said shaft is correspondingly elastically bent on an entire length of the lancet.

11. A lancet coupling mechanism for an apparatus for obtaining and analyzing a blood sample, comprising:
a lancet having a sharp tip configured to pierce a body part and a rear end located opposite the sharp tip;
at least one chamber, which extends in a direction of a piercing axis, wherein the chamber contains the lancet;
a drive rod, which penetrates into the chamber for coupling onto the lancet, in order to execute a controlled forward and reverse movement of the lancet along the piercing axis;
at least one bending axis of the lancet that extends transverse to the piercing axis; wherein the lancet is elastically bendable from a relaxed state to a bent state around the bending axis;
wherein at least in a rear area of the chamber comprises a shaft that has at least one curvature that curves around the bending axis;
wherein the shaft guides the controlled forward and reverse movement of the lancet;
wherein the curvature at the rear area of the chamber is configured to bend the rear end of the lancet from the relaxed state to the bent state; and
the drive rod is configured to engage the bent rear end onto the lancet when the lancet is in the bent state, and the drive rod has a formfitting connection to the lancet when the lancet is in the relaxed state.

12. The lancet coupling mechanism according to claim 11, wherein:
the lancet has at least one coupling recess;
the drive rod has at least one coupling structure on a front end; and
the coupling structure of the drive rod extends perpendicularly to the bending axis of the lancet and engages in the coupling recess of the bent lancet when the lancet moves forward.

13. The lancet coupling mechanism according to claim 12, wherein:
the coupling recess includes at least one eye located in an area of the rear end of the lancet;
the lancet is manufactured from a piece of level flat sheet metal; and
the coupling structure of the drive rod includes at least one hook, for hooking into the eye, on the front end of the drive rod.

14. The lancet coupling mechanism according to claim 13, wherein:
the lancet includes a body;
the body of the lancet comprises two arms, which are implemented as mirror images; and the eye includes at least two eyes that are provided at the end of the two arms, respectively.

15. The lancet coupling mechanism according to claim 14, wherein one of the two arms is bent elastically upward around the bending axis extending transversely to the piercing axis, while the other of the two arms is bent elastically downwards in the opposite direction.

16. The lancet coupling mechanism according to claim 15, wherein the chamber comprises a right shaft and a left shaft, one shaft being curved upward and the other shaft being curved downward.

17. The lancet coupling mechanism according to claim 11, wherein the shaft has a central guide groove, whose height and width are adapted to the dimensions of the drive rod.

18. The lancet coupling mechanism according to claim 11, wherein the shaft has a rectangular cross section having a height which is greater than a thickness of the lancet, which is slidable back and forth with play in the shaft.

19. The lancet coupling mechanism according to claim 11, wherein the drive rod is manufactured from a single piece of sheet steel.

20. The lancet coupling mechanism according to claim 11, wherein the shaft is curved over an entire length of the shaft around the bending axis; and
the lancet inserted into said shaft is correspondingly elastically bent on an entire length of the lancet.

* * * * *